(12) United States Patent
Takeuchi et al.

(10) Patent No.: US 6,824,269 B2
(45) Date of Patent: Nov. 30, 2004

(54) EYE'S OPTICAL CHARACTERISTIC MEASURING SYSTEM

(75) Inventors: Gaku Takeuchi, Tokyo-to (JP); Katsuhiko Kobayashi, Tokyo-to (JP); Masahiro Shibutani, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 54 days.

(21) Appl. No.: 09/972,318

(22) Filed: Oct. 5, 2001

(65) Prior Publication Data

US 2002/0047993 A1 Apr. 25, 2002

(30) Foreign Application Priority Data

Oct. 10, 2000 (JP) ........................................ 2000/309484

(51) Int. Cl.[7] ................................................ A61B 3/10
(52) U.S. Cl. ...................................... 351/214; 351/211
(58) Field of Search ................................. 351/205, 206, 351/207, 211, 212, 214, 221; 600/558

(56) References Cited

U.S. PATENT DOCUMENTS

| | | | | |
|---|---|---|---|---|
| 4,743,107 A | * | 5/1988 | Aizu et al. .................. | 351/211 |
| 4,952,049 A | * | 8/1990 | Matsumoto .................. | 351/211 |
| 5,559,321 A | * | 9/1996 | Kusaka ..................... | 250/201.8 |
| 5,579,063 A | * | 11/1996 | Magnante et al. ........... | 351/211 |
| 6,234,978 B1 | * | 5/2001 | Mihashi et al. ............. | 600/558 |
| 6,270,221 B1 | * | 8/2001 | Liang et al. ................ | 351/221 |
| 6,296,358 B1 | * | 10/2001 | Cornsweet et al. .......... | 351/206 |

\* cited by examiner

*Primary Examiner*—Brian L. Casler
*Assistant Examiner*—John R. Sanders
(74) *Attorney, Agent, or Firm*—Nields & Lemack (57) ABSTRACT

An eye's optical characteristic measuring system comprises an aperture diaphragm 14 arranged at a position approximately conjugate to a pupil of an eye 1 under testing and for determining regions to pass a light beam on the pupil 18, a projection optical system 2 for projecting a primary index image on a fundus of the eye under testing via the aperture diaphragm, a photodetection optical system 3 for forming a secondary index image on a photoelectric detector 21 via the aperture diaphragm by a reflected light beam from the fundus of the eye under testing, and detecting units 26, 27 and 28 for detecting a light amount intensity distribution of the secondary index image based on a signal from the photoelectric detector.

3 Claims, 9 Drawing Sheets

| No.1 | S:-2, C:-1.25, Ax:9° |
| No.2 | S:-2.25, C:-1, Ax:10° |
| No.3 | S:-2.5, C:-0.75, Ax:11° |
| No.4 | S:-2.5, C:-1, Ax:10° |

FIG.8

Ixy = Oxy * Pxy     Oxy     Ixy

EYE'S OPTICAL CHARACTERISTIC MEASURING SYSTEM

BACKGROUND OF THE INVENTION

The present invention relates to an eye's optical characteristic measuring system for measuring an optical characteristic of an ocular optical system by measuring a light amount intensity distribution on an index image, which is projected to an ocular fundus of an eye under testing.

In the past, an eye's optical characteristic measuring system has been known. In this conventional type system, an index image such as a pinhole image is projected to a fundus of an eye under testing, and the index image is formed on a photoelectric detector according to a reflected light beam. Based on a light amount intensity distribution characteristic of the index image, a point image light amount intensity distribution function to indicate an optical characteristic of the ocular optical system is determined.

In this eye's optical characteristic measuring system, the light amount intensity distribution of the target image formed by a light beam passing through the optical system of the eye is directly measured, and the eye's optical characteristic of the eye under testing can be accurately measured. The target image formed on the fundus of the eye under testing can also be obtained by calculation as a simulation image. The eye's optical characteristic obtained by the eye's optical characteristic measuring system can be utilized as an information useful for an ophthalmological treatment or for a correction of visual acuity.

Also, currently, a new surgical operation on a cornea using a laser beam to correct visual acuity is being emerged. In this operation, shape of the surface of the cornea itself is processed by the laser beam. Accordingly, for the purpose of performing a preoperative measurement and a postoperative evaluation to determine the amount of this processing, it is necessary to accurately determine the eye's optical characteristic in different regions on a pupil.

However, in the conventional type system as described above, the measurement is made by using the light beam with a certain fixed aperture on the pupil of the eye under testing, and the measurement can be made only on the eye's optical characteristic for a certain fixed pupil diameter, and it is disadvantageous in that the eye's optical characteristic in different regions on the pupil cannot be obtained.

SUMMARY OF THE INVENTION

It is an object of the present invention to overcome the disadvantages of the conventional type eye's optical characteristic measuring system as described above, and to provide an eye's optical characteristic measuring system, by which it is possible to determine a distribution of an eye's optical characteristic on different regions on a pupil and over the total region on the pupil.

To attain the above object, the eye's optical characteristic measuring system according to the present invention comprises an aperture diaphragm arranged at a position approximately conjugate to a pupil of an eye under testing and for determining regions to pass a light beam on the pupil, a projection optical system for projecting a primary index image on a fundus of the eye under testing via the aperture diaphragm, a photodetection optical system for forming a secondary index image on a photoelectric detector via the aperture diaphragm by reflected light beam from the fundus of the eye under testing, and a detecting unit for detecting a light amount intensity distribution of the secondary index image based on a signal from the photoelectric detector. Also, the present invention provides an eye's optical characteristic measuring system as described above, wherein the aperture diaphragm is designed to enable to change an aperture. Further, the present invention provides an eye's optical characteristic measuring system as described above, wherein the aperture diaphragm is designed in such manner that a position of an aperture can be changed. Also, the present invention provides an eye's optical characteristic measuring system as described above, wherein the aperture diaphragm comprises a plurality of aperture plates, and the reflected a light beam can be divided into a plurality of regions by combining the aperture plates. Further, the present invention provides an eye's optical characteristic measuring system as described above, wherein a light amount intensity distribution of a secondary index image is detected for each of the regions, there is provided a display unit for displaying an eye's optical characteristic obtained from the result of the detection, and the display unit displays an aspect of division of the regions and displays the eye's optical characteristic for each of the divided regions.

BRIEF DESSCRIPTION OF THE DRAWINGS

FIG. 5 represents diagrams each showing a light amount intensity distribution obtained by a measurement in the present embodiment.

DETAILED DESCRIPTION OF THE PREFERRED EMBODIMENT

Description will be given below on an embodiment of the present invention.

Figure 1:
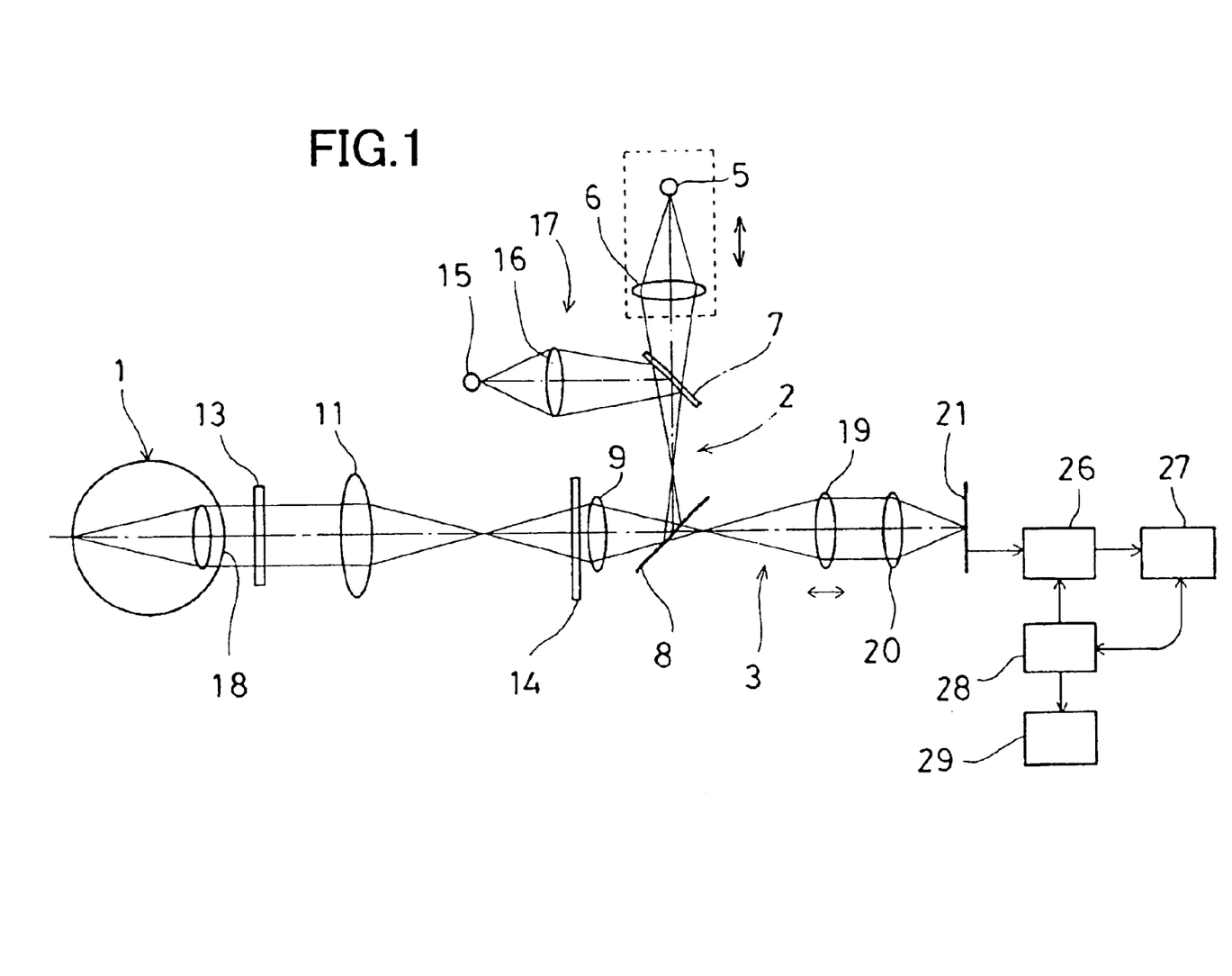
FIG. 1 is a schematical drawing to show an optical system of an embodiment of the present invention.

Referring to FIG. 1, description will be given on an optical system of an embodiment of the present invention;

In the figure, a reference numeral 1 denotes an eye under testing, a reference numeral 2 denotes a projection optical system, and a reference numeral 3 denotes a photodetection optical system.

The projection optical system 2 comprises a light source 5, a projection lens 6 for converging a projected light beam emitted from the light source 5, a half-mirror 7 arranged on an optical axis of the projection lens 6, a polarization beam splitter 8 for reflecting the projected laser beam passing through the half-mirror 7 and for projecting a linearly polarized light component (S linear polarized light) of a first polarization direction toward the eye 1 under testing, a relay lens 9 disposed on a projection light axis of the polarization beam splitter 8 from the direction of the polarization beam splitter 8, an objective lens 11, a ¼ wave plate, and an aperture diaphragm 14 arranged at a position approximately conjugate (including conjugate position) to a pupil 18 of the eye 1 under testing. Further, there are provided a fixed target system 17 having a fixed target 15 and a condenser lens 16 facing toward the half-mirror 7. The light source 5 and the fixed target 15 are at positions conjugate to an ocular fundus of the eye 1 under testing. As to be described later, each of the light source 5 and the fixed target 15 forms an image at the ocular fundus. The light source 5 and the projection lens 6 are integrally designed, and these can be moved together with a focusing lens 19 along an optical axis as described later.

In common with the projection optical system 2 the photodetection optical system 3 shares: the polarization beam splitter 8, the relay lens 9 disposed on the projection light axis of the polarization beam splitter 8, the objective lens 11, and the ¼ wave plate 13.

On the optical axis of the reflection light passing through the polarization beam splitter 8, there are provided the focusing lens 19 and an image forming lens 20. The focusing lens 19 can be moved along the optical axis of the reflection light. The image forming lens 20 forms the reflected light beam as an image on a photoelectric detector 21, which is disposed at a position conjugate to the fundus of the eye 1 under testing.

A photodetection signal from the photoelectric detector 21 is stored at a storage unit 27 via a signal processing unit 26. Writing of data from the signal processing unit 26 to the storage unit 27 is controlled by a control unit 28. Based on the data stored at the storage unit 27, the control unit 28 performs required calculations, and the result of the calculation is displayed on a display unit 29.

Figure 2A:
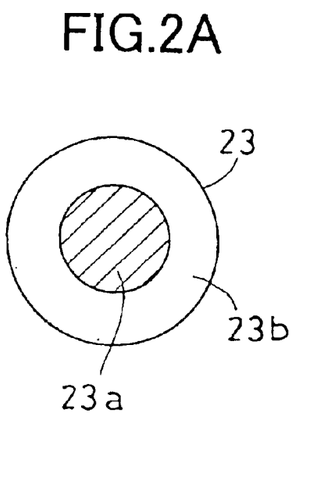
FIG. 2 represents drawings to explain an aperture diaphragm to be used in the embodiment.
Figure 2B:
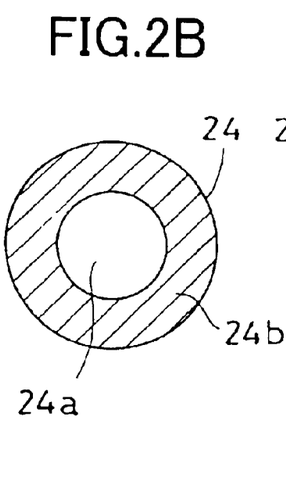

Description will be given on the aperture diaphragm 14 referring to FIG. 2(A), FIG. 2(B), and FIG. 2(C).

The aperture diaphragm 14 comprises three circular aperture plates 23, 24 and 25. The aperture plate 23 has a circular light shielding portion 23a at the center, and a peripheral annular portion serves as a transmitting portion 23b. The aperture plate 24 comprises a transmitting portion 24a in the same shape as the light shielding portion 23a and an annular light shielding portion 24b in the same shape as the transmitting portion 23b. In the aperture plate 25, two small fan-shaped portions are arranged at symmetrical positions, each having central angle of 45° as formed by dividing the circle in 8 equal parts, and these two small fan-shaped portions serve as transmitting portions 25a and 25a. The remaining two large fan-shaped portions serve as light shielding portions 25b and 25b.

Figure 3:
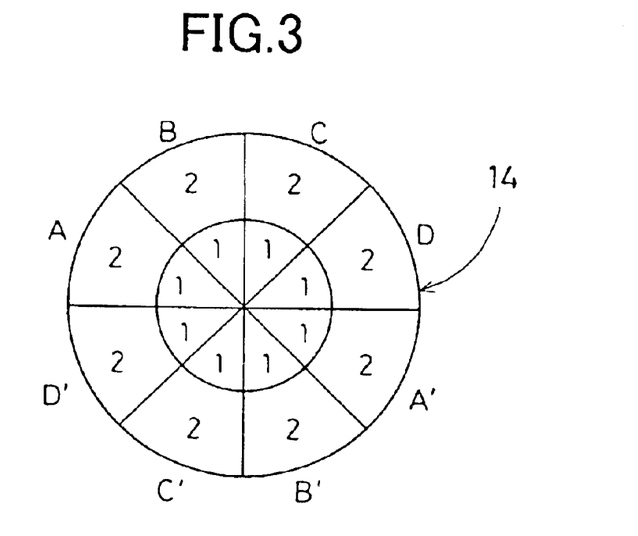
FIG. 3 is a drawing to show status of regions divided by the aperture diaphragm.

By combining the aperture plates 23, 24 and 25 together, as shown in FIG. 3, apertures of A1, A2, B1, B2, C1, C2, D1 and D2, and also, apertures of A'1, A'2, B'1, B'2, C'1, C'2, D'1 and D'2 can be obtained.

Figure 2C:
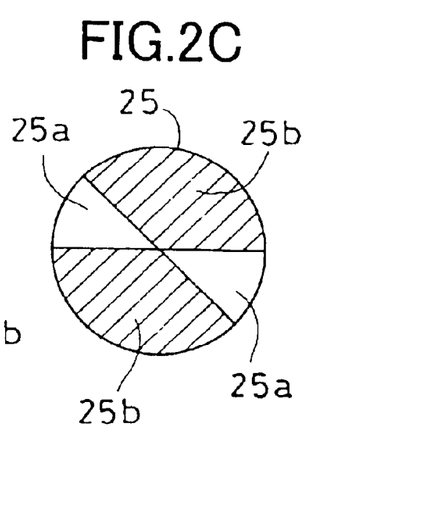

For instance, when the aperture plate 25 is set to the condition shown in FIG. 2(C) and the aperture plate 23 is combined with the aperture plate 25, the apertures A2 and A'2 can be obtained. When the aperture plate 24 is combined with the aperture plate 25, the apertures A1 and A'1 can be obtained.

Further, when the aperture plate 25 is rotated step by step each time at an angle of 45° and is combined with the aperture plates 23 and 24 at each step, it is possible to obtain the apertures A1, A2, B1, B2, C1, C2, D1 and D2, and also, the apertures A'1, A'2, B'1, B'2, C'1, C'2, D'1 and D'2.

In the following, operation of the above optical system is described.

A subject person with the eye 1 under testing is instructed to gaze at the fixed target 15, and the projection beam is projected by the projection optical system 2. A visible light is used for the fixed target 15, and an infrared light is used for the projection beam.

The projection light beam (infrared light) from the light source 5 passes through the projection lens 6 and the half-mirror 7 and reaches the polarization beam splitter 8. Then, the S linearly polarized light component is reflected by the polarization beam splitter 8, and this passes through the relay lens 9. It is projected to the fundus of the eye 1 under testing by the objective lens 11 via the ¼ wave plate 13, and a primary index image is formed.

When the S linearly polarized light passes through the ¼ wave plate, the S linearly polarized light is turned to a right circularly polarized light. The projected light beam is reflected at the fundus of the eye 1 under testing. When the reflected light beam is reflected by the fundus, the reflected light beam is turned to a left circularly polarized light. Further, when the reflected light beam passes through the ¼ wave plate 13, the reflected light beam is turned to a P linearly polarized light, which has direction of polarization deviated by an angle of 90° from a direction of the S linearly polarized light.

The P linearly polarized light is guided toward the polarization beam splitter 8 by the objective lens 11 and the relay lens 9. The polarization beam splitter 8 reflects the S linearly polarized light and transmits the P linearly polarized light. Thus, the reflected light beam transmits the polarization beam splitter 8, and the reflected light beam is formed as a secondary index image on the photoelectric detector 21 by the focusing lens 19 and the image forming lens 20.

The light amount intensity distribution of the secondary index image, which is received by the photoelectric detector 21, reflects the eye's optical characteristic of the eye 1 under testing. By detecting the light receiving condition of the photoelectric detector 21, the eye's optical characteristic can be measured.

Next, not all of the projected light beam projected to the fundus of the eye 1 under testing is necessarily reflected on the fundus of the eye 1 under testing. A part of the light beam enters through the surface into superficial layer of the fundus and scattering reflection occurs (the so-called bleeding reflection) (hereinafter referred as "scattering reflection"). When this scattering reflection is received together with the reflected light beam at the photoelectric detector 21, the scattering reflection is turned to a noise in the light amount intensity distribution of the secondary index image, and it is not possible to accurately measure the eye's optical characteristic of the ocular optical system.

Polarizing status of the light beam by such scattering reflection is in a random state. For this reason, when the light beam passes through the ¼ wave plate 13 and is turned to a linearly polarized light, only a limited part of the light beam matches with the P linearly polarized light. Therefore, almost all of the scattering reflection light components are absorbed by the polarization beam splitter 8, and the light beam received by the photoelectric detector 21 is a projected reflection light beam, from which the scattering reflection light components have been substantially removed. When the ¼ wave plate 13 is used as a component element of the projection optical system 2 and the photodetection optical system 3, it is possible to measure the accurate eye's optical characteristic of the ocular optical system.

Figure 4:
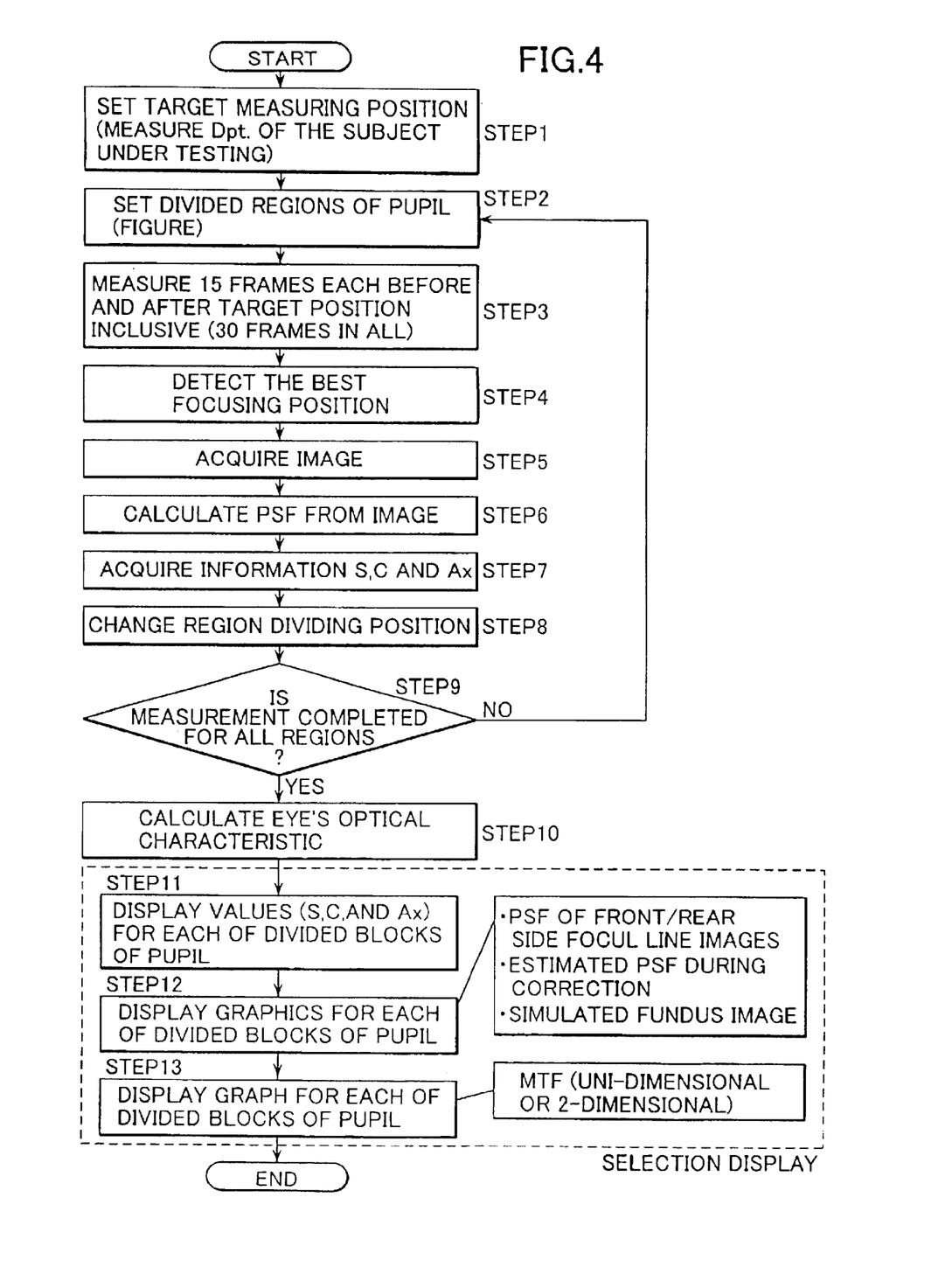
FIG. 4 is a flow chart showing operation of the embodiment of the present invention.

Now, description will be given on the measurement of the eye's optical characteristic of the eye under testing referring to FIG. 3 and FIG. 4.

In the measurement of the eye's optical characteristic, the pupil 18 is divided into a number of regions as required. For each of the regions thus divided, the eye's optical characteristic of the region is measured, and the eye's optical characteristic of the eye under testing is determined according to the regional eye's optical characteristic thus obtained.

(Step01) While the subject person under testing is instructed to gaze at the fixed target 15, and the focusing lens 19 is moved. In association with the movement of the focusing lens 19, the light source 5 and the projection lens 6 are integrally moved. Focusing is performed roughly, and a target measuring position corresponding to the refractive power of the eye under testing is set. This setting can be performed in such a method that the setting is performed based on the result of measurement by an objective refractometer determined in advance. Or, this setting can be performed in such a method that the subject person observes the index image displayed on a monitor based on a signal from the photoelectric detector 21 and the focusing is performed so that rough focusing can be made on the target image.

(Step02) The region to be measured is set by the aperture diaphragm 14. The setting is performed by combining the aperture plates 23, 24, and 25. To set a region of A1 as shown in FIG. 3, the aperture plate 25 is turned to the condition shown in FIG. 2(C), and the aperture plate 24 is superimposed on the aperture plate 25, and the region of A1 can be set. The reflected light beam reflected by the fundus of the eye 1 under testing passes through a region which is symmetrical to A1 of the aperture diaphragm 14. Thus, the aperture A'1 is opened.

The projected light beam from the light source 5 passes through only the region A1. The aperture diaphragm 14 is at a position conjugate to the pupil 18, and the projected light beam passes through a region, which corresponds to the region A1 in the pupil 18. The reflected light beam reflected by the fundus of the eye 1 under testing passes through the region of A'1, which is symmetrical to the region A1 of the aperture diaphragm 14 and reaches the polarization beam splitter 8. Then, the reflected light beam passes through the polarization beam splitter 8. As described above, only the P linearly polarized light passes through the polarization beam splitter 8, and the scattering light included in the reflection light beam is almost completely removed. The reflected projection light beam passing through only the region A1 of the pupil 18 is reflected by the fundus of the eye 1 under testing. The reflected reflection light beam passes through the region A'1 and is projected on the photoelectric detector 21 by the focusing lens 19 and the image forming lens 20, and a secondary index image is formed.

(Step03) Under this condition, the position as set in Step 1 is used as the center, and the focusing lens 19 is moved before and after the center by a predetermined amount of step. In association with the movement of the focusing lens 19, the light source 5 and the projection lens 6 are integrally moved. While changing the focusing condition on the photoelectric detector 21, an image signal obtained at the photoelectric detector 21 is stored in the storage unit 27 (e.g. frame memory) at each step. The image signals to be stored are, for instance, the signals for 30 frames including the target position (target focusing position).

(Step04) The control unit 28 compares a large number of image data stored at the storage unit 27. If the eye under testing has astigmatism, there are two focusing positions at a front side focal line position and at a rear side focal line position of the eye under testing. Thus, the data of focusing conditions such as positions of the focusing lens 19 at the focusing at the front side focal line position and the rear side focal line position are acquired.

(Step05) The control unit 28 selects two image data, i.e. the data at the front side focal line position and the rear side focal line position of the eye under testing. In this case, at the front side focal line position and the rear side focal line position, the index image is focused only in the predetermined direction and these are formed as slit-like images different from each other in the direction. As a result, the two image data at the front side focal line position and the rear side focal line position are judged and selected according to whether the form of the index image is in a slit-like shape or not.

(Step06) Based on the two image data at the front side focal line position and the rear side focal line position selected in Step 5, the light amount intensity distribution at each position is calculated at the control unit 28. Further, from the light amount intensity distribution at each position, the 2-dimensional light amount intensity distribution (PSF: spread function) is calculated.

Now, brief description will be given on the 2-dimensional light amount intensity distribution referring to FIG. 5.

Figure 5A:
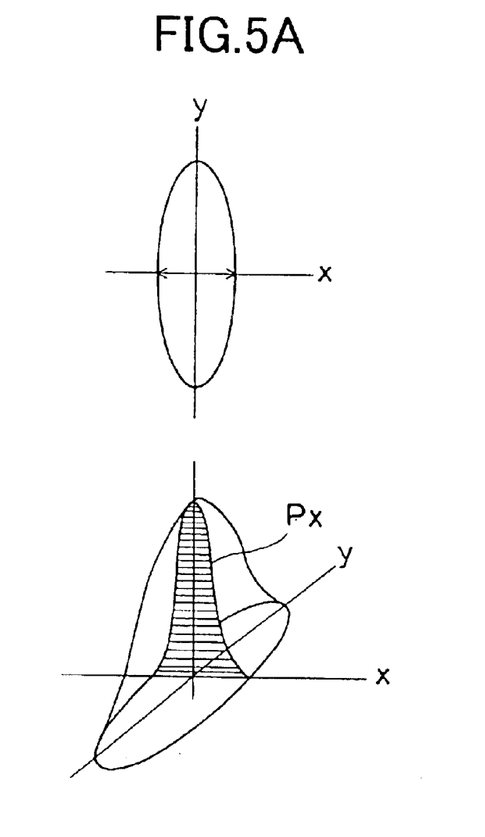
FIG. 5(A) represents diagrams each showing the light amount intensity distribution on a rear side focal line.
Figure 5B:
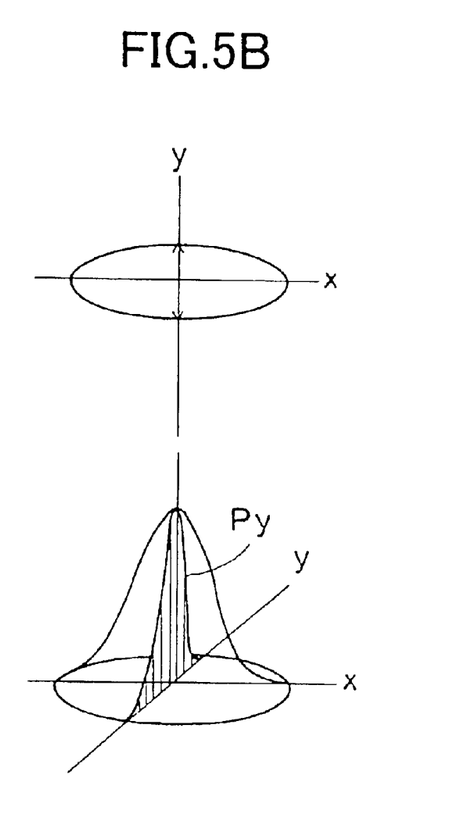
FIG. 5(B) represents diagrams each showing the light amount intensity distribution on a front side focal line.

The light amount intensity distribution at the rear side focal line is shown in FIG. 5(A), and the light amount intensity distribution at the front side focal line position is given in FIG. 5(B).

In the light amount intensity distribution at the rear side focal line as shown in FIG. 5(A), Px, i.e. a cross-section in X direction, shows the light amount distribution in a direction where the light beam is most converged on rear side focal line.

Similarly, in the light amount intensity distribution of the front side focal line as shown in FIG. 5(B), Py, i.e. a cross-section in Y direction, shows the light amount distribution in a direction where the light beam is most converged on the front side focal line.

Figure 6A:
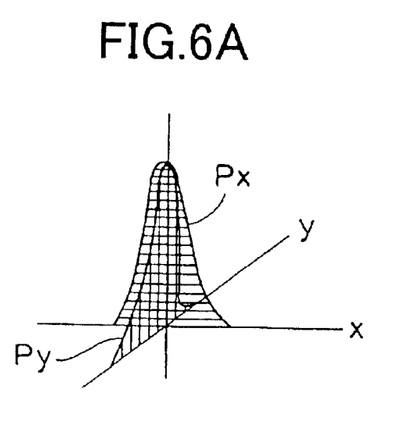
FIG. 6(A) is a diagram showing the light amount intensity distribution on a rear side focal line, and FIG. 6 (B) is a diagram showing 2-dimensional light amount intensity distribution obtained from the light amount intensity distribution on a front side focal line.
Figure 6B:
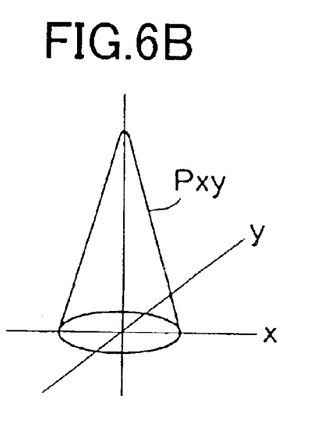

The 2-dimensional light amount intensity distribution (PSF: spread function) can be given as shown FIG. 6(A) and FIG. 6(B) by elliptical approximation at a light amount intensity I (i). For instance, in FIG. 6(B), the 2-dimensional light amount intensity distribution is calculated as Pxy.

(Step07) Information data S, C, and Ax (a spherical degree, an astigmatic degree, and an astigmatic axis) of the eye under testing in the region A1 are acquired by calculation based on the positional data of the focusing lens 19, the directions of the slit images at the front side focal line position and the rear side focal line position, and the 2-dimensional light amount intensity distribution Pxy.

The difference of the positions of the focusing lens 19 at the front side focal line position and at the rear side focal line position corresponds to the astigmatic degree C, and the position of the focusing lens 19 at the rear side focal line position corresponds to the spherical degree S. From the directions a of the slit images, the astigmatic axis can be obtained.

(Step08) Next, the aperture plate 24 is replaced with the aperture plate 23. By replacing with the aperture plate 23, the region is turned to A2 (referring to FIG. 3).

(Step09) For the region A2, which is the region to be measured next, it is judged whether the measurement has been performed or not. If the measurement is not performed yet, it is returned to Step 2, and resetting of the region is carried out. Then, the procedures up to Step08 are performed. As long as there is a region not measured yet, it is returned to Step02, and the procedures up to Step08 are repeatedly performed.

(Step09) It is judged whether the measurements have been completed in all of the regions or not. When the measurements in all regions have been completed, it should proceed to Step 10.

(Step 10) Based on the results of measurements in all regions, the eye's optical characteristic is calculated.

As shown in Step06, the value of Pxy can be obtained from the light amount intensity distribution on the rear side focal line and the light amount intensity distribution on the front side focal line. The value of Pxy is obtained when the projected light beam passes through the ophthalmo-optical system of the eye 1 under testing twice. Thus, the following relationship exists between the value of Pxy and spread function (PSF) P'xy of the ophthalmo-optical system of the eye 1 under testing:

$$Pxy=(P'xy)^2$$

Therefore, P'xy=√(Pxy). Accordingly, by obtaining Pxy, spread function (PSF), i.e. P'xy, of the ophthalmo-optical system of the eye 1 under testing can be obtained.

Figure 8:
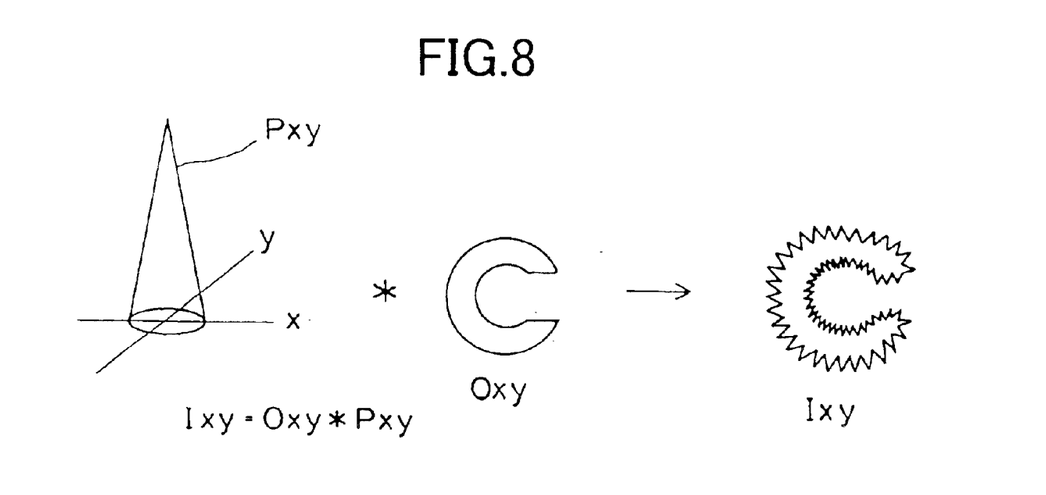
FIG. 8 represents drawings to explain a index and a corrected image.

As described above, Pxy thus obtained is superimposed and integrated with the index Oxy, which the eye 1 under testing actually sees, as shown in FIG. 8. Then, an image Ixy can be obtained. The image Ixy represents an image of the fundus of the eye under testing, which is obtained when the eye 1 under testing is corrected by a spectacle lens, which combines a spherical lens of refractive power-S diopter with a cylindrical lens of refractive power-diopter.

Here, when a Fourier transform is represented by FT and an inverse Fourier transform is represented by IFT,
  pxy=FT (Pxy)
  oxy=FT (Oxy)
  ixy=FT (Ixy)
Then, from:
  ixy=pxy×oxy, and
  Ixy=IFT (ixy),
the image Ixy can be obtained.

Further, the Fourier transform is performed on PSF as described above, and MTF (modulating transfer function) is obtained. When MTF is given for the regions A1, A2, D1 and D2, it is as shown in FIG. 11(A), FIG. 11(B), FIG. 11(C) and FIG. 11(D) respectively. In FIG. 11, each of the axis of ordinate represents intensity of spectrum (frequency), and it is normalized to 1. Each of the axis of abscissa represents frequency.

In the procedure of Step 11 and after, the results of measurements obtained for each of the regions are displayed. Or, based on the measurement results, calculations are made as necessary, and the results of calculations are displayed.

Figure 7:
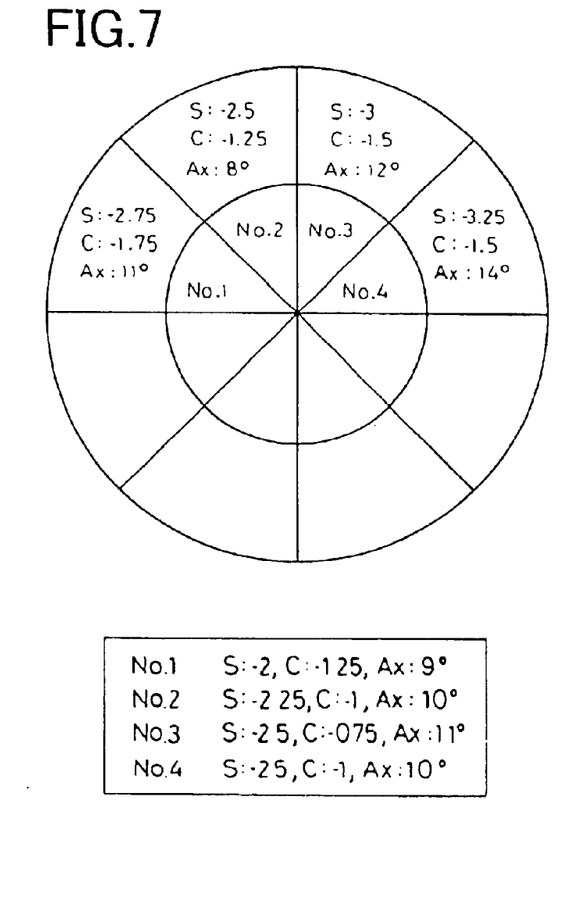
FIG. 7 is a drawing to show an aspect of divided regions of a pupil and data of eye's optical characteristic of each of the divided regions.

(Step 11) The status of divided regions of the pupil 18 is displayed, and the regional characteristics (S, C, and Ax) are displayed for each region. The display for each region is superimposed on division status of the pupil 18, or it is shown in form of a table (referring to FIG. 7).

(Step 12) For each of the divided regions, graphics are displayed.

Figure 9:
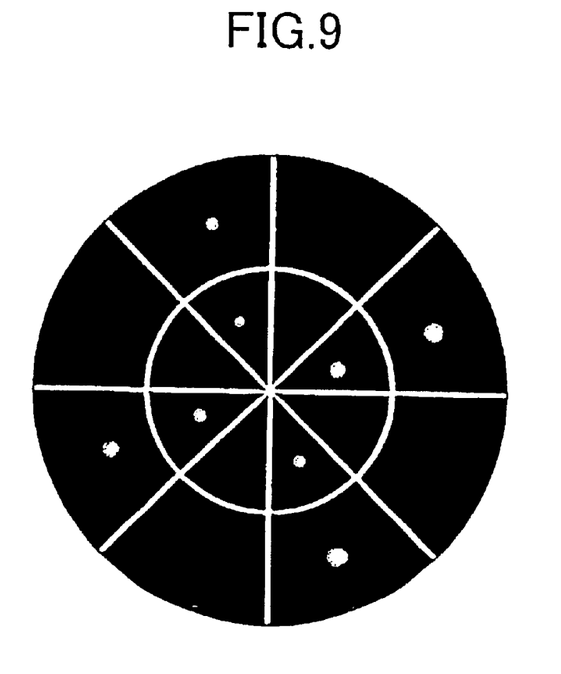
FIG. 9 is a drawing to explain estimated PSF during correction of visual acuity.
Figure 10:
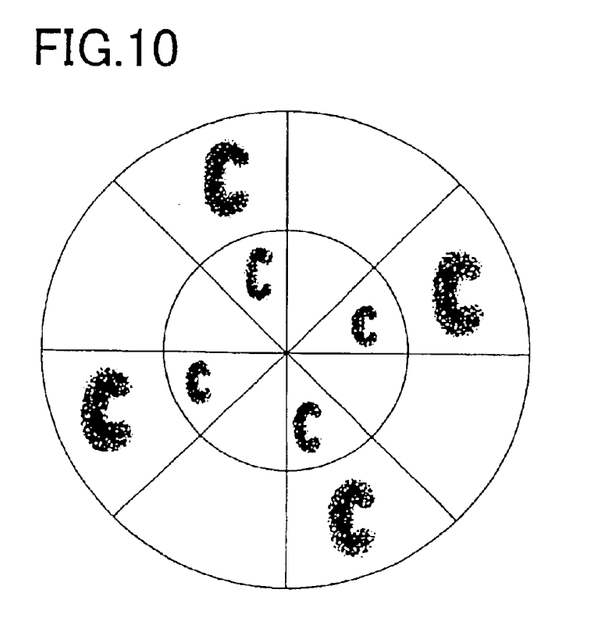
FIG. 10 is a drawing to explain a simulation image during correction of visual acuity.
Figure 11A:
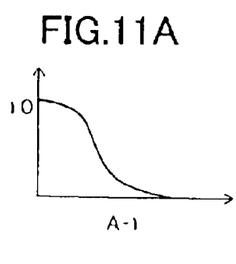
FIG. 11(A), FIG. 11(B), FIG. 11(C) and FIG. 11(D) each represents a diagram of MTF obtained from the measured light amount intensity distribution.
Figure 11B:
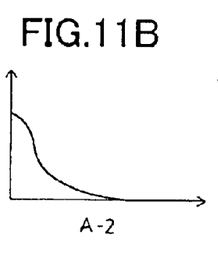
Figure 11C:
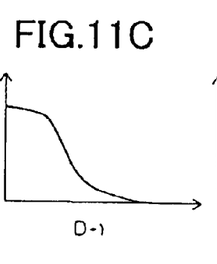
Figure 11D:
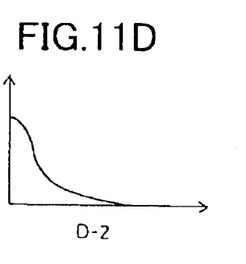

In the graphics on the display, the following data are displayed: PSF (Px, Py) at the front side focal line position and the rear side focal line position (FIG. 5(A) and FIG. 5(B)), estimated value of Pxy at correction (FIG. 9), simulated fundus image (Ixy) (FIG. 10).

(Step 13) For each of the divided regions, a graph is displayed.

Figure 12:
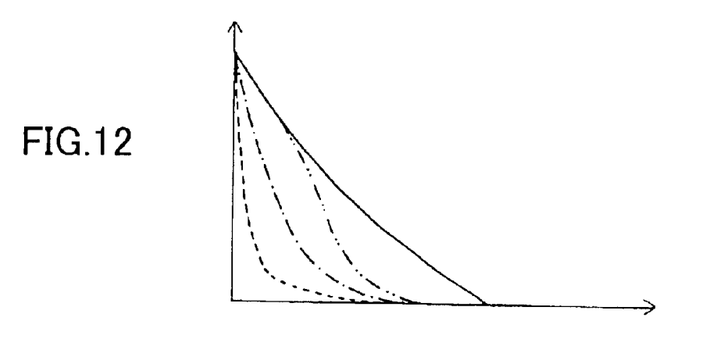
FIG. 12 is a diagram obtained by superimposing the MTF and shown as a single diagram.

The graphs on the display are MTP as described above. The graphs shown in FIG. 11 are independently displayed for each region. Or, as shown in FIG. 12, the graphs are displayed as different types of lines for each region and are superimposed.

As a result, the eye's optical characteristic is obtained for each of the divided regions of the pupil 18.

Figure 13:
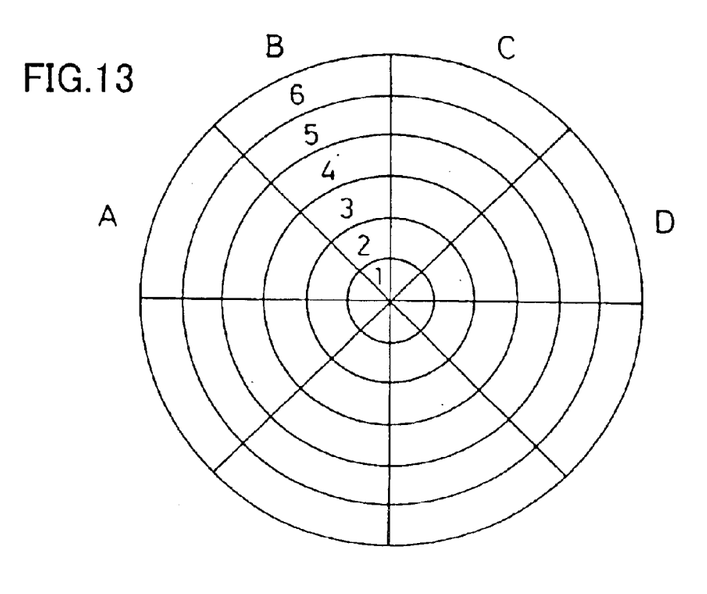
FIG. 13 is a drawing to show another aspect of division.

The regional division should be made by an adequate aspect of division depending upon the purpose of the measurement. For instance, as shown in FIG. 13, the total region may be divided into 4 equal parts in a circumferential direction (A–D) and divided in 6 parts with equal spacing in a radial direction. For the regions divided further, the eye's optical characteristic may be measured.

Figure 14:
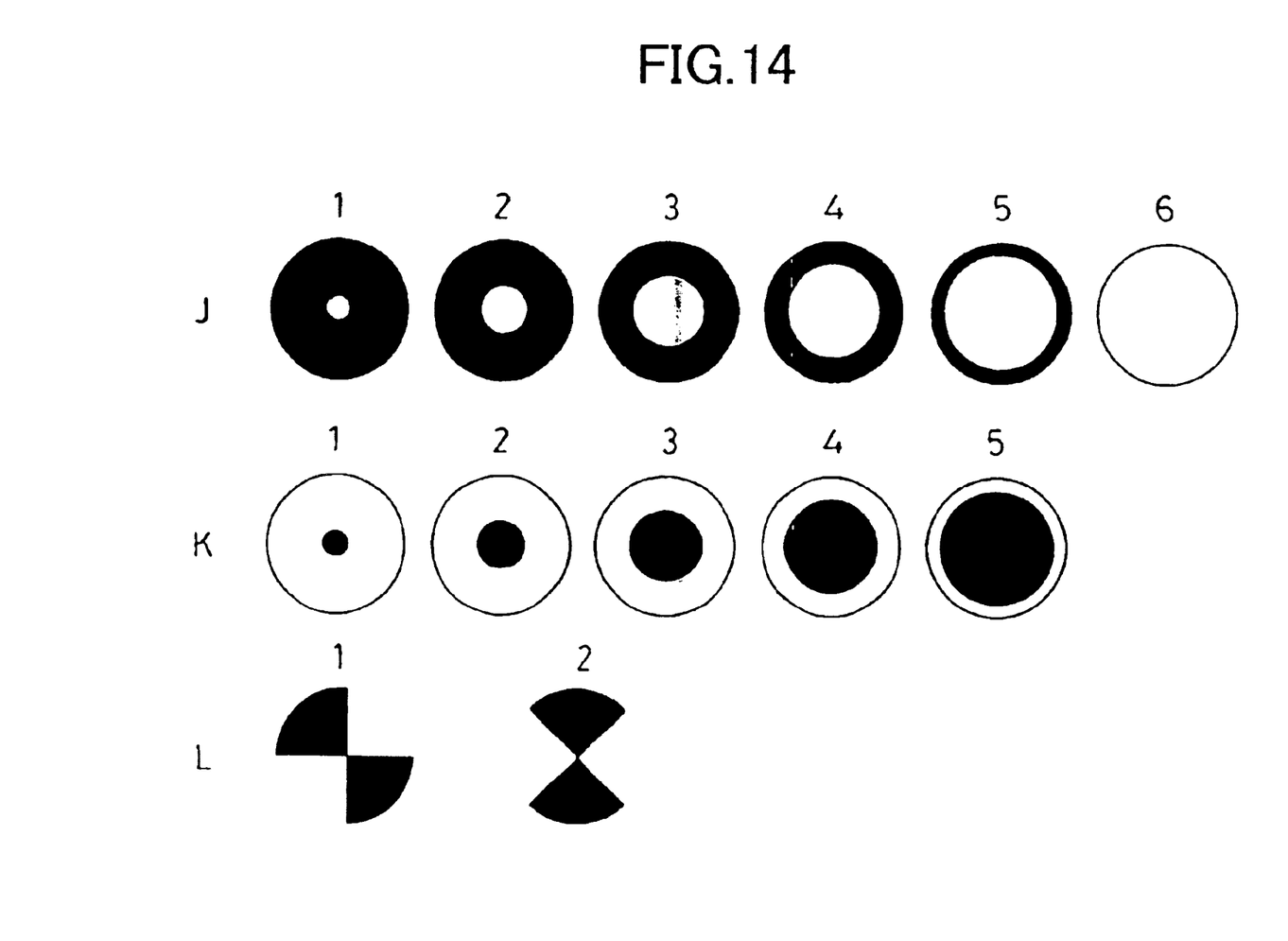
FIG. 14 represents drawings to explain aperture diaphragm to be used in the above aspect of division.

To obtain the aspect of division as shown in FIG. 13, the total region can be divided by combining central aperture plates J1–J6, peripheral aperture plates K1–K5, and fan-shaped aperture plates L1 and L2 as shown in FIG. 14. For instance, by combining the central aperture plate J3, the peripheral aperture plate K2, and the fan-shaped aperture plates L1 and L2 at the positions as shown in the figure, the region D3 in FIG. 13 can be obtained.

Figure 15:
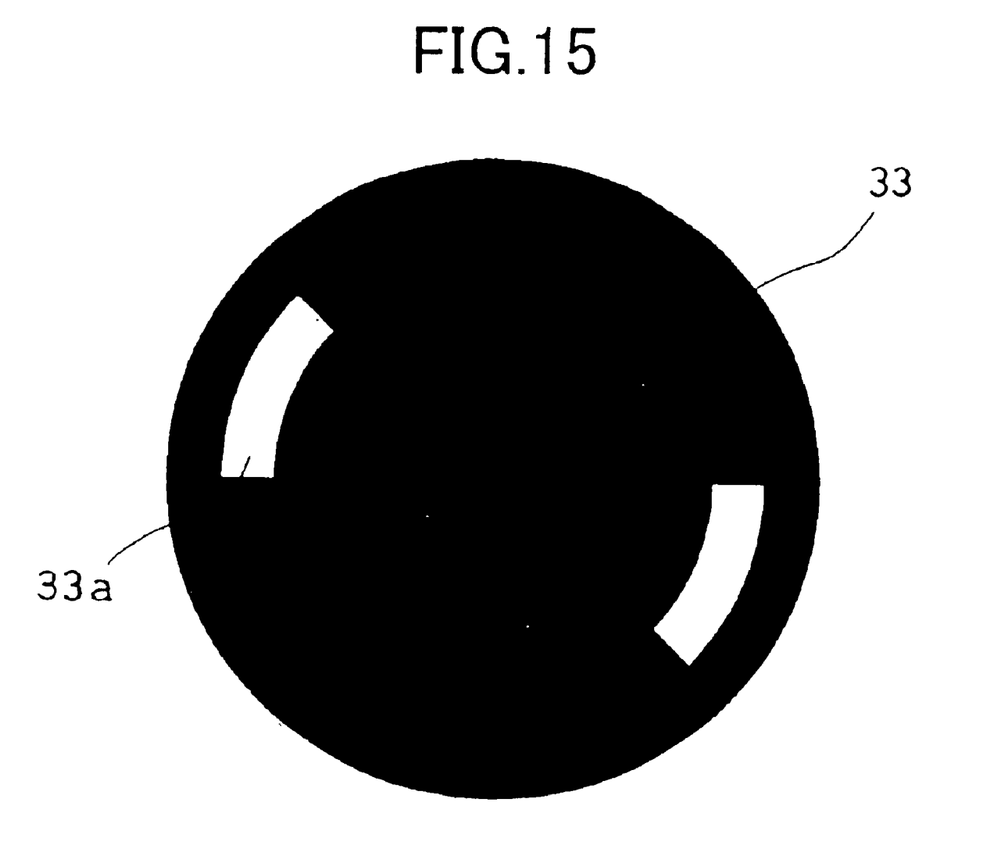
FIG. 15 is a drawing to explain another type of aperture diaphragm.

Further, as shown in FIG. 15, an aperture plate 33 may be used where apertures 33a are formed only for the regions to be obtained. In FIG. 15, only one aperture plate 33 is shown, while 6 aperture plates may be used, each of which has an aperture deviated in a radial direction. By rotating the same aperture plate 33 by a step of 45°, regions positioned on the same circumference, e.g. A5, B5, C5 and D5, can be obtained.

In the above embodiment, the divided regions are formed in an arc shape, while the regions may be divided in annular shape. For instance, by using the aperture plates 23 and 24 as shown in FIG. 2, it is possible to divide into 2 regions, i.e. central and peripheral regions. Division in an annular shape is advantageous in that the eye's optical characteristic corresponding to enlargement and shrinking of an iris can be obtained.

In the above embodiment, the polarization beam splitter is used, while the beam splitter may be replaced with a half-mirror, and polarizing plates having directions of polarization deviated by 90° from each other may be provided on optical paths of the projection system and the photodetection system.

According to the present invention, in an eye's optical characteristic measuring system comprising an aperture diaphragm arranged at a position approximately conjugate to a pupil of an eye under testing and for determining regions to pass a light beam on the pupil, a projection optical system for projecting a primary index image on a fundus of the eye under testing via the aperture diaphragm, a photodetection optical system for forming a secondary index image on a photoelectric detector via the aperture diaphragm by a reflected light beam from the fundus of the eye under testing, and a detecting unit for detecting a light amount intensity distribution of the secondary index image based on a signal from the photoelectric detector, the aperture diaphragm is designed to enable to change an aperture. As a result, the eye's optical characteristic can be measured for a plurality of different regions on the pupil, and important information can be obtained for the operation such as corneal correction surgery or orthokeratology.

What is claimed is:

1. An eye's optical characteristic measuring system, comprising an aperture diaphragm arranged at a position approximately conjugate to a pupil of an eye under testing and for determining regions to pass a light beam on the pupil, a projection optical system for projecting a primary index image on a fundus of the eye under testing via said aperture diaphragm, a photodetection optical system for forming a secondary index image on a photoelectric detector via said aperture diaphragm by a reflected light beam from the fundus of the eye under testing, and a detecting unit for detecting a light amount intensity distribution of the secondary index image based on a signal from said photoelectric detector, wherein said projection optical system has a first optical axis, said photodetection optical system has a second optical axis, said first optical axis shares a part in common with said second optical axis, said aperture diaphragm is positioned at said shared part on the optical axes and has at least two apertures, wherein said apertures have a symmetrical relation with respect to said optical axes, and positions of said apertures can be changed.

2. The eye's optical characteristic measuring system according to claim 1, wherein said aperture diaphragm comprises a plurality of aperture plates, and said reflected light beam can be divided into a plurality of regions by combining said aperture plates.

3. The eye's optical characteristic measuring system according to claim 2, wherein a light amount intensity distribution of a secondary index image is detected for each of said regions, there is provided a display unit for displaying an eye's optical characteristic obtained from the result of the detection, and said display unit displays an aspect of division of the regions and displays the eye's optical characteristic for each of the divided regions.

* * * * *